(12) United States Patent
Ng et al.

(10) Patent No.: US 11,505,587 B2
(45) Date of Patent: Nov. 22, 2022

(54) METHOD OF PREPARING A KERATIN-BASED BIOMATERIAL AND KERATIN-BASED BIOMATERIAL FORMED THEREOF

(71) Applicant: Nanyang Technological University, Singapore (SG)

(72) Inventors: Kee Woei Ng, Singapore (SG); Pietradewi Hartrianti, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 409 days.

(21) Appl. No.: 14/761,868

(22) PCT Filed: Jan. 15, 2014

(86) PCT No.: PCT/SG2014/000016
§ 371 (c)(1),
(2) Date: Jul. 17, 2015

(87) PCT Pub. No.: WO2014/112950
PCT Pub. Date: Jul. 24, 2014

(65) Prior Publication Data
US 2015/0368308 A1    Dec. 24, 2015

Related U.S. Application Data

(60) Provisional application No. 61/754,218, filed on Jan. 18, 2013.

(51) Int. Cl.
| | | |
|---|---|---|
| A61K 8/65 | (2006.01) | |
| A61K 8/73 | (2006.01) | |
| C08B 37/04 | (2006.01) | |
| C07K 14/47 | (2006.01) | |
| C08B 37/00 | (2006.01) | |
| C08H 1/06 | (2006.01) | |
| C08L 33/00 | (2006.01) | |
| C08B 37/08 | (2006.01) | |
| C07K 1/10 | (2006.01) | |

(52) U.S. Cl.
CPC ........... *C07K 14/4741* (2013.01); *C07K 1/10* (2013.01); *C08B 37/003* (2013.01); *C08B 37/0072* (2013.01); *C08B 37/0084* (2013.01); *C08H 1/06* (2013.01); *C08L 33/00* (2013.01)

(58) Field of Classification Search
CPC .............................. A61K 38/015; A61K 47/36
See application file for complete search history.

(56) References Cited

U.S. PATENT DOCUMENTS

| | | | | |
|---|---|---|---|---|
| 3,642,498 | A * | 2/1972 | Anker | A23P 20/10 106/156.1 |
| 5,567,293 | A * | 10/1996 | Paleologou | B01D 61/44 204/523 |
| 6,372,244 | B1 * | 4/2002 | Antanavich | A61F 2/022 424/422 |
| 6,685,838 | B2 * | 2/2004 | Licata | B01D 15/00 210/661 |
| 2003/0049299 | A1 * | 3/2003 | Malaviya | A61B 17/064 424/423 |
| 2005/0124797 | A1 * | 6/2005 | Kelly | C07K 14/4741 530/357 |
| 2008/0004423 | A1 * | 1/2008 | Kelly | C08F 261/04 528/373 |
| 2009/0042169 | A1 * | 2/2009 | Kintrup | A23G 3/362 433/217.1 |
| 2009/0069541 | A1 * | 3/2009 | Kelly | C08J 9/28 530/357 |
| 2009/0197316 | A1 * | 8/2009 | Johnson | A61K 47/6929 435/187 |
| 2012/0010726 | A1 * | 1/2012 | Bluecher | A61B 17/0057 623/23.72 |
| 2012/0104656 | A1 * | 5/2012 | Kelly | C08H 1/06 264/330 |
| 2013/0172197 | A1 * | 7/2013 | Kokoris | C12Q 1/6869 506/2 |
| 2013/0274190 | A1 * | 10/2013 | Wang | A61L 15/425 514/9.4 |
| 2015/0080552 | A1 * | 3/2015 | Burnett | C07K 14/4741 530/357 |

FOREIGN PATENT DOCUMENTS

| | | | | |
|---|---|---|---|---|
| WO | 03/018673 | 3/2003 | | |
| WO | 2005/028560 | 3/2005 | | |
| WO | WO-2008040357 | A1 * | 4/2008 | ............... C08H 1/06 |

OTHER PUBLICATIONS

Gan L.M. (2011) Developing a novel suturing material using human hair proteins, pp. 1-2.*

(Continued)

*Primary Examiner* — David Steadman
(74) *Attorney, Agent, or Firm* — Seed Intellectual Property Law Group LLP

(57) ABSTRACT

Method of preparing a keratin-based biomaterial is provided. The method comprises a) reacting keratin with a polymer having at least one of an amine and carboxylic functional group in the presence of a carbodiimide cross-linking agent to form a cross-linked keratin-polymer material; and b) freeze drying the cross-linked keratin-polymer material to form the keratin-based bio-material. A keratin-based biomaterial thus prepared is also provided.

9 Claims, 13 Drawing Sheets

(56) References Cited

OTHER PUBLICATIONS

Hamasaki et al. (2008) Fabrication of highly porous keratin sponges by freeze-drying in the presence of calcium alginate beads, Materals Sci. Eng. C, vol. 28, pp. 1250-1254.*

Wrzesniewska-Tosik (2008) Fibrous Keratin-Containing Composite, Fibers Textil. Eastern Europe J.,vol. 16, No. 6(71), pp. 113-116.*

Reham B.H.A. (2009) "Alginates: Biology and Applications", Microbiol. Monographs vol. 13, (Editor Rehm B.H.A.), Springer publish.*

Balaji et al., "Preparation and comparative characterization of keratin-chitosan and keratin-gelatin composite scaffolds for tissue engineering applications," *Materials Science and Engineering C* 32:975-982, 2012.

Balaji et al., "Characterization of keratin-collagen 3D scaffold for biomedical applications," *Polym. Adv. Technol.* 23:500-507, 2012.

Hamasaki et al., "Fabrication of highly porous keratin sponges by freeze-drying in the presence of calcium alginate beads," *Materials Science and Engineering C* 28:1250-1254, 2008.

Hill et al., "Some properties of keratin biomaterials: Kerateines," *Biomaterials* 31:585-593, 2010.

Hong et al., "Development of a Bio-Based Composite Material from Soybean Oil and Keratin Fibers," *J. Appl. Polym. Sci.* 95:1524-1538, 2005.

Min et al., "Electrospinning of silk fibroin nano fibers and its effect on the adhesion and spreading of normal human keratinocytes and fibroblasts in vitro," *Biomaterials* 25:1289-1297, 2004.

Park et al., "Characterization of porous collagen/hyaluronic acid scaffold modified by 1-ethyl-3-(3-dimethylaminopropyl)carbodiimide cross-linking," *Biomaterials* 23:1205-1212, 2002.

Park et al., "Biological characterization of EDC-crosslinked collagen-hyaluronic acid matrix in dermal tissue restoration," *Biomaterials* 24:1631-1641, 2003.

Rho et al., "Electrospinning of collagen nanofibers: Effects on the behavior of normal human keratinocytes and early-stage wound healing," *Biomaterials* 27:1452-1461, 2006.

Richter et al., "Mechanisms of hepatocyte attachment to keratin biomaterials," *Biomaterials* 32:7555-7561, 2011.

Rouse et al., "A Review of Keratin-Based Biomaterials for Biomedical Applications," *Materials* 3:999-1014, 2010.

Saul et al., "Keratin hydrogels support the sustained release of bioactive ciprofloxacin," *J. Biomed. Mater. Res. Part A* 98A:544-553, 2011.

Sierpinski et al., "The use of keratin biomaterials derived from human hair for the promotion of rapid regeneration of peripheral nerves," *Biomaterials* 29:118-128, 2008.

Srinivasan et al., "Porous Keratin Scaffold-Promising Biomaterial for Tissue Engineering and Drug Delivery," *J. Biomed. Mater. Res. Part B: Appl. Biomater.* 92B:5-12, 2010.

Tanabe et al., "Preparation and characterization of keratin-chitosan composite film," *Biomaterials* 23:817-825, 2002.

Wang et al., "The effect of gelatin-chondroitin sulfate-hyaluronic acid skin substitute on wound healing in SCID mice," *Biomaterials* 27:5689-5697, 2006.

Wang et al., "Human keratin hydrogels support fibroblast attachment and proliferation in vitro," *Cell Tissue Res.* 347:795-802, 2012.

Wenk et al., "Silk fibroin as a vehicle for drug delivery applications," *Journal of Controlled Release* 750:128-141, 2011.

Zhang et al., "Preparation of collagen-chondroitin sulfate-hyaluronic acid hybrid hydrogel scaffolds and cell compatibility in vitro," *Carbohydrate Polymers* 84:118-125, 2011.

* cited by examiner a) 1 mM b) 5 mM c) 10 mM d) 50 mM e) 100 mM a) 1 mM b) 5 mM c) 10 mM d) 50 mM e) 100 mM (a)

(b)

(a)

(i)

(ii)

(b)

(i)

(ii)

(a)

(b)

(c)

| | | | |
|---|---|---|---|
| | | Day 5 (4x) |  |
| Day 1 (4x) |  | Day 5 (10x) |  |
| Day 3 (4x) |  | Day 7 (4x) |  |
| Day 3 (10x) |  | Day 7 (10x) |  |

METHOD OF PREPARING A KERATIN-BASED BIOMATERIAL AND KERATIN-BASED BIOMATERIAL FORMED THEREOF

CROSS-REFERENCE TO RELATED APPLICATION

This application claims the benefit of priority of U.S. provisional application No. 61/754,218 filed on 18 Jan. 2013, the content of which is incorporated herein by reference in its entirety for all purposes.

TECHNICAL FIELD

The invention relates to methods of preparing keratin-based biomaterials, and keratin-based biomaterials formed thereof.

BACKGROUND

Protein-based biomaterials have been explored for many biomedical applications due to their ability to function as a synthetic extracellular matrix that facilitates cell-cell and cell-matrix interactions.

Even though clinically relevant biomaterials or templates have been prepared by combining a material of human origin and an established material for biomedical purposes, they are either very limited in supply or very expensive. Examples include blood-extracted fibrin, such as Tisseel from Baxter, and recombinant human extracellular matrix proteins. As a result, products of clinical relevance currently in use are generally made with materials of animal origin, which can result in undesirable immunological reactions or preclude groups of patients due to cultural or religious constraints.

In this regard, proteins, such as collagen, albumin, gelatin, fibroin and keratin, have been investigated in developing naturally-derived biomaterials. Of these, keratin-based biomaterials have shown great promise due to their biocompatibility, biodegradability, natural abundance, and their ability to self-assemble, promote cell attachment and support cell binding.

Keratin may also be fabricated into a number of physical forms suitable for biomaterial applications, such as coatings, foams, sponges, and hydrogels. Previous studies have shown that keratin is able to support cell attachment, cell proliferation, and provide sustained release delivery of drugs. These previous studies suggested that keratin may be useful for tissue engineering, regenerative medicine and drug delivery purposes.

Notwithstanding the above, keratin has poor physical and mechanical characteristics compared to other naturally derived biomaterial such as collagen. Improving properties of keratin-based biomaterials may, therefore, present new and clinically relevant applications.

Several attempts have been made to improve properties of keratin, such as physical blending with materials such as chitosan, gelatin and collagen. Even though these methods appear to have improved mechanical properties of the final keratin-based biomaterials, the amount of partner material required is significantly large compared to those of keratin.

Further, even though particulate-leaching methods may be used to produce 3D porous templates, due to difficulties in leaching out porogens from thick templates, however, only thin templates may be produced. Other techniques, such as wet spinning, may be used to prepare keratin fibres. These techniques, however, require specialized equipment and further processing, such as knitting or braiding, to produce porous templates.

In view of the above, there remains a need for an improved method to prepare keratin-based biomaterials that overcomes or at least alleviates one or more of the above-mentioned problems.

SUMMARY

In a first aspect, the invention relates to a method of preparing a keratin-based biomaterial. The method comprises:
  a) reacting keratin with a polymer having at least one of an amine and carboxylic functional group in the presence of a carbodiimide cross-linking agent to form a cross-linked keratin-polymer material; and
  b) freeze drying the cross-linked keratin-polymer material to form the keratin-based biomaterial.

In a second aspect, the invention relates to a keratin-based biomaterial prepared by a method according to the first aspect.

BRIEF DESCRIPTION OF THE DRAWINGS

The invention will be better understood with reference to the detailed description when considered in conjunction with the non-limiting examples and the accompanying drawings, in which.

$$\text{Cross-linking index (\%)} = \left[\frac{NH_o - NH_t}{NH_o}\right] \times 100$$

where $NH_o$ is amount of free amino groups in the sample before cross-linking; $NH_t$ is amount of free amino groups in the sample after cross-linking. In the embodiment shown, increasing EDC concentration correlated to higher degrees of cross-linking, reaching a plateau of about 80% at 50 mM EDC.

Figure 2:
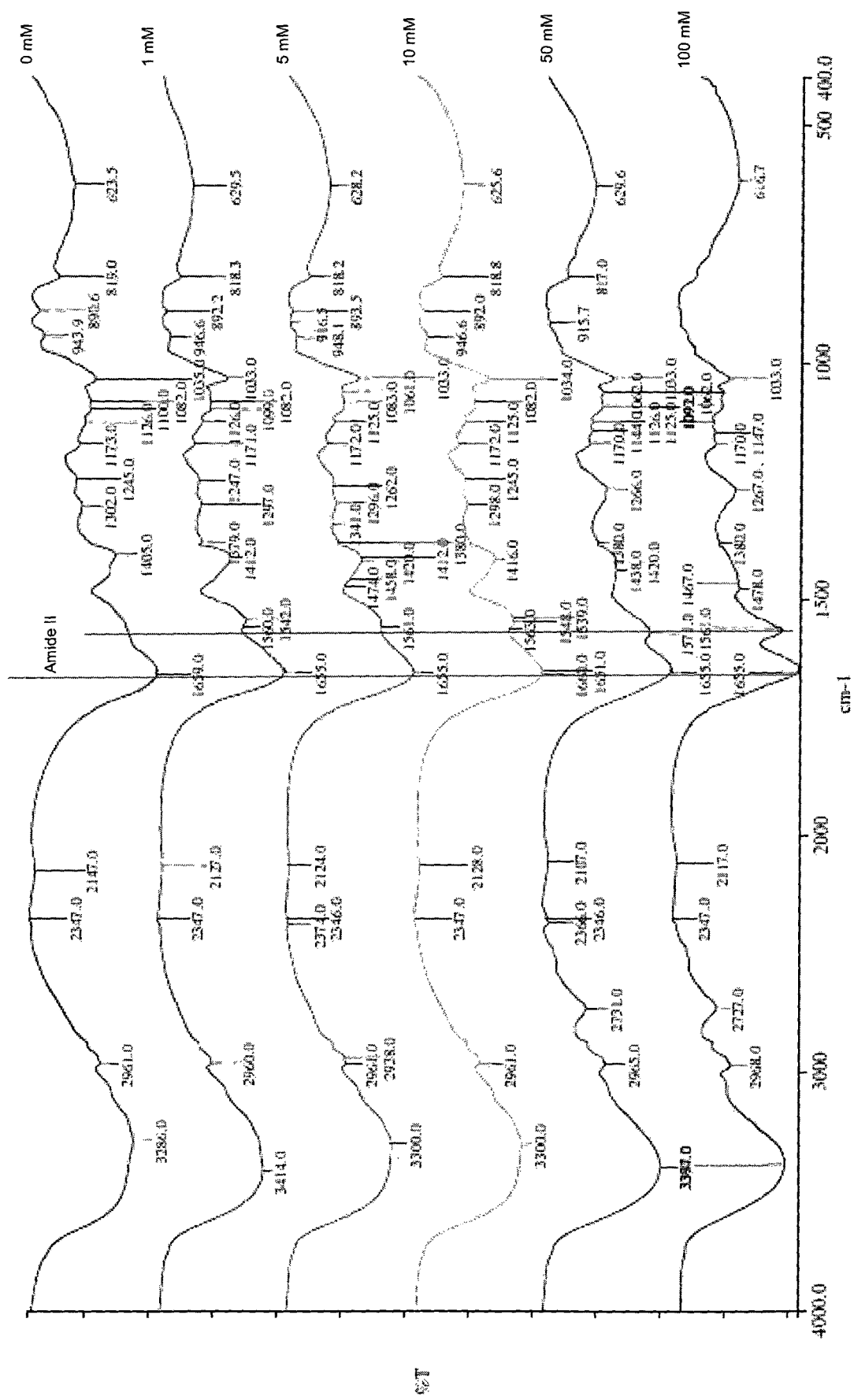

FIG. 2 is a graph showing Fourier Transform Infrared Spectroscopy (FTIR) spectra of cross-linked keratin alginate for keratin to alginate ratio of 1:1 by weight at different EDC concentration. Increasing amide band intensities confirmed the increase in degree of cross-linking with increasing EDC concentration.

Figure 3:
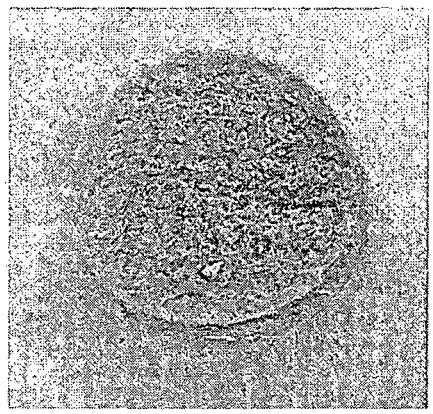
Figure 3:
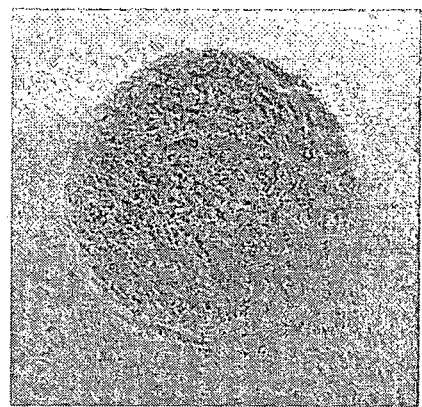
Figure 3:
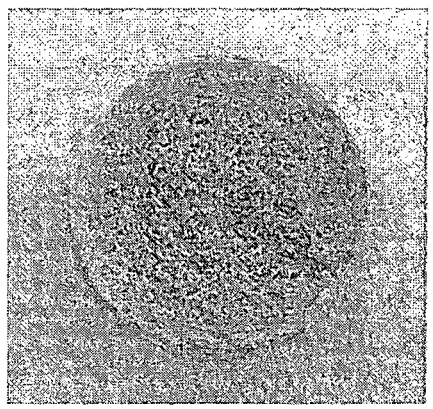
Figure 3:
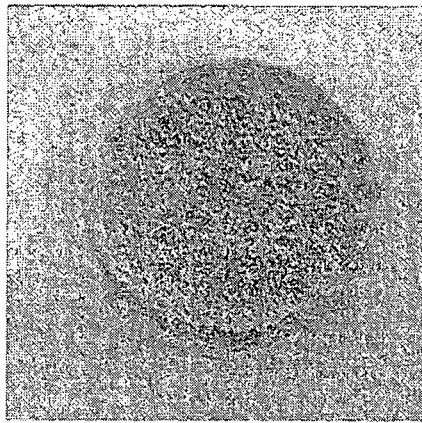
Figure 3:
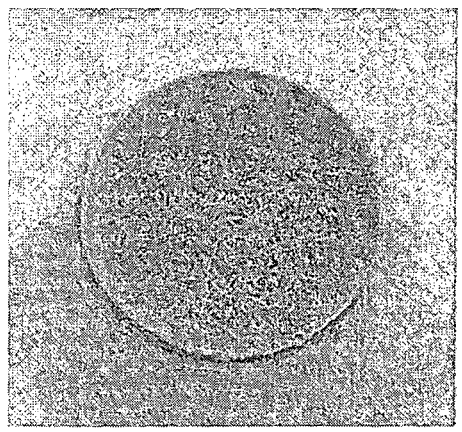

FIG. 3 shows photographs depicting macroscopic appearance of cross-linked keratin-alginate sponges for keratin to alginate ratio of 1:1 by weight at different EDC concentrations of (a) 1 mM; (b) 5 mM; (c) 10 mM; (d) 50 mM; and (e) 100 mM. All samples were stable and took the shape of the holding vessel.

Figure 4:
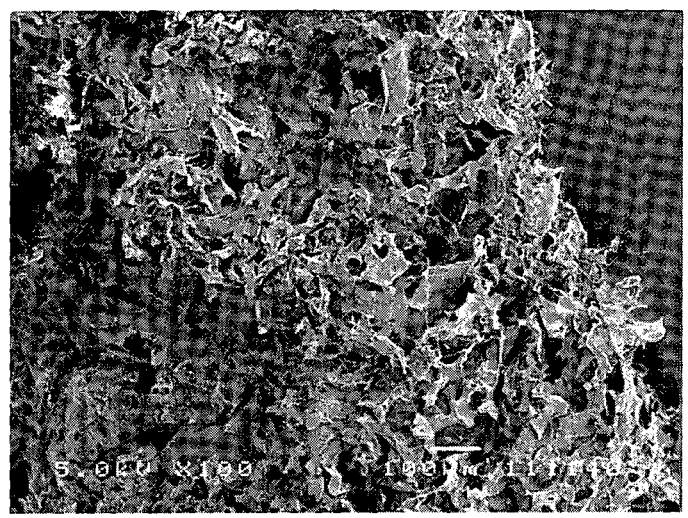
Figure 4:
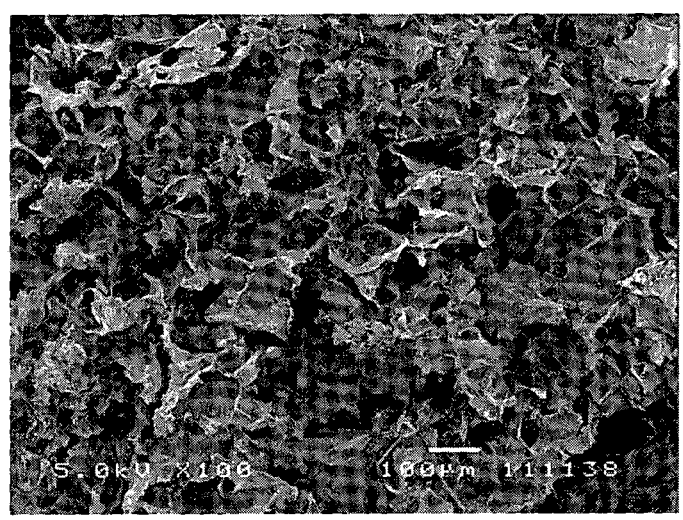
Figure 4:
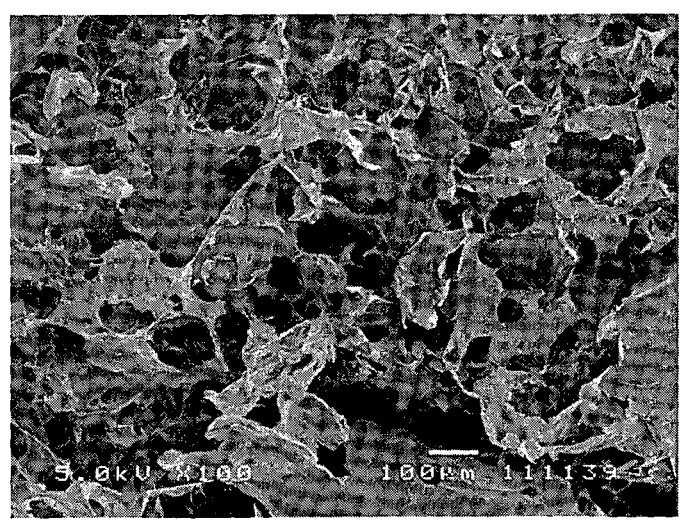
Figure 4:
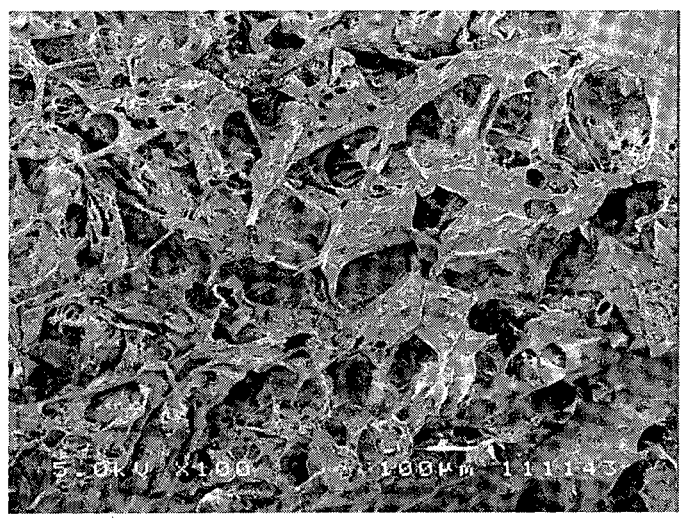
Figure 4:
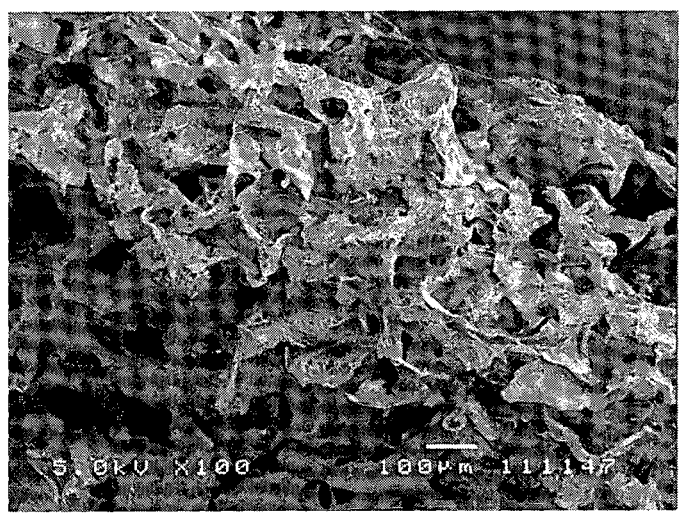

FIG. 4 shows Scanning Electron Microscopy (SEM) images of cross-linked keratin-alginate sponges for keratin to alginate ratio of 1:1 by weight at different EDC concentrations of (a) 1 mM; (b) 5 mM; (c) 10 mM; (d) 50 mM; and (e) 100 mM. All samples had microporous architectures with pore spaces that were highly interconnected. Scale bar in the figures denote a length of 100 µm.

Figure 5:
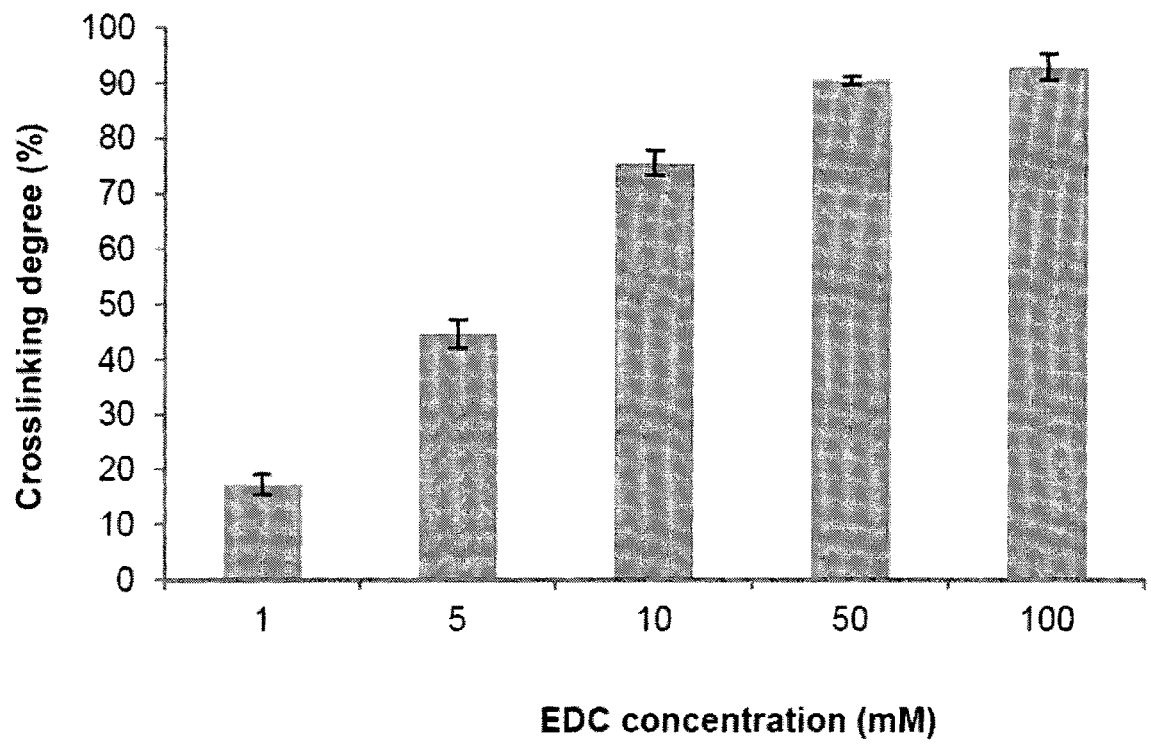
Figure 5:
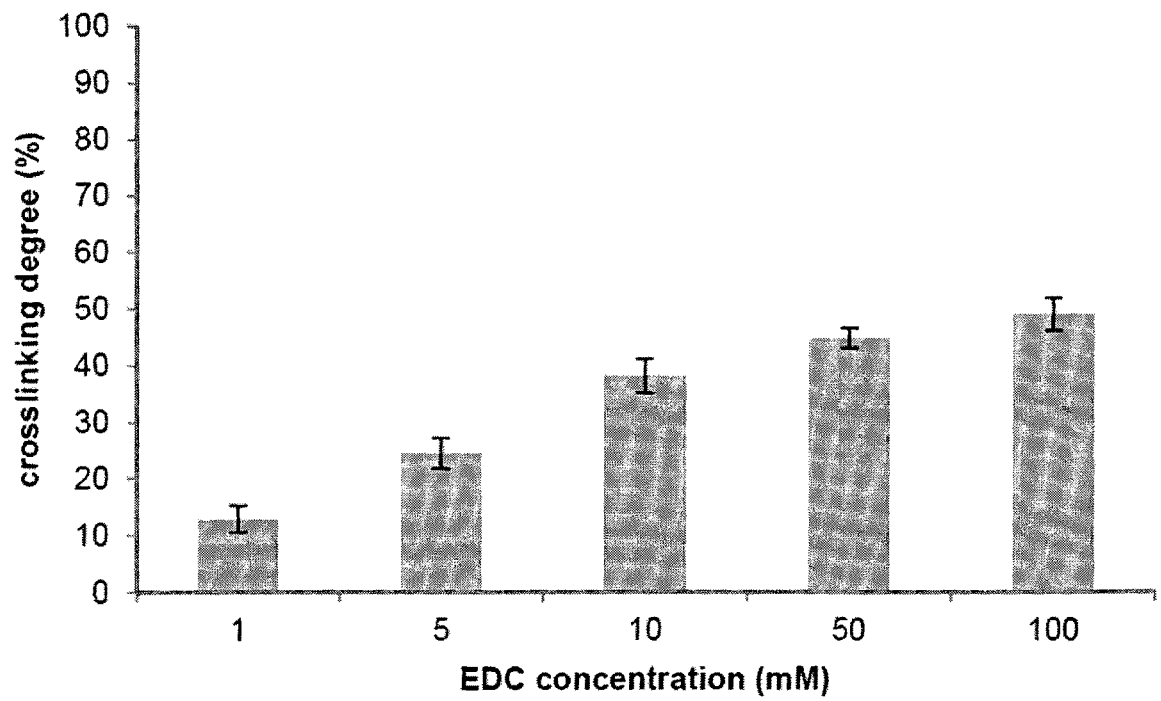

FIG. 5 depicts graphs of crosslinking index of crosslinked keratin-alginate sponges with different concentration of EDC (1 mM to 100 mM) based on (a) free amine group determination; and (b) carboxylic group determination, according to an embodiment. Crosslinking degree was calculated based on the amount of crosslinked groups divided by sum of free and crosslinked groups. The calculated values were different for amine and carboxylic acid groups as there were different amounts of the respective groups to begin with. Results showed that the higher the EDC concentration used, the lower the remaining free amine and carboxylic acid groups compared to the non-crosslinked mixture, indicating that crosslinking degree increased with increasing amount of crosslinkers used. The results also showed that most of the amine groups have formed amide bonds with carboxylic groups, while there were still free carboxylic groups available. This shows, for example, that there are more carboxylic acid groups in the mixture.

Figure 6:
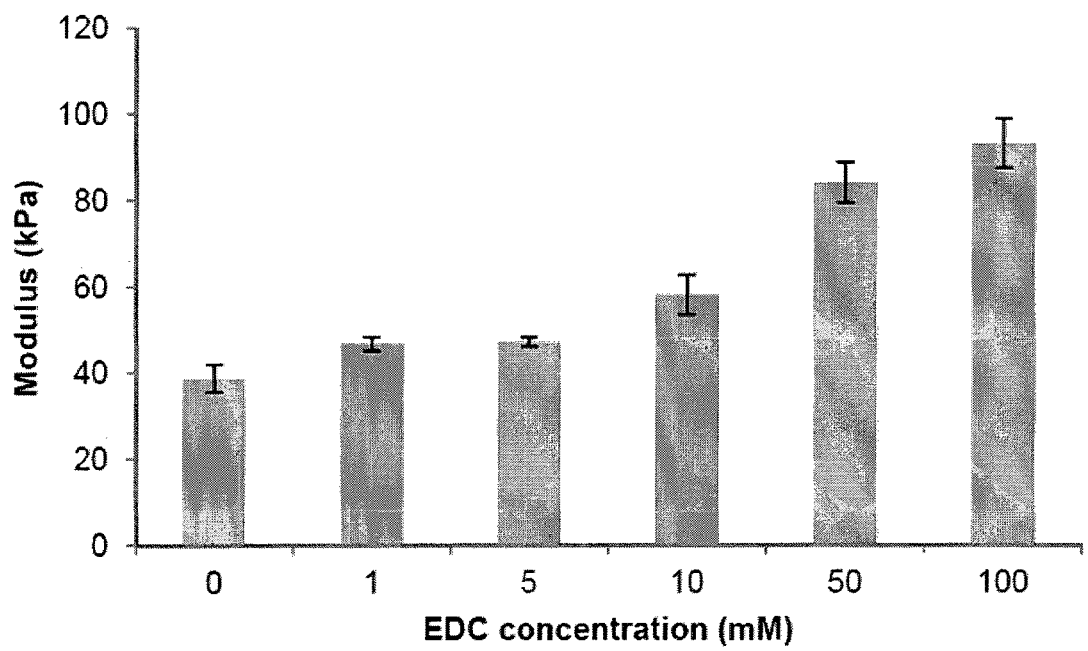
Figure 6:
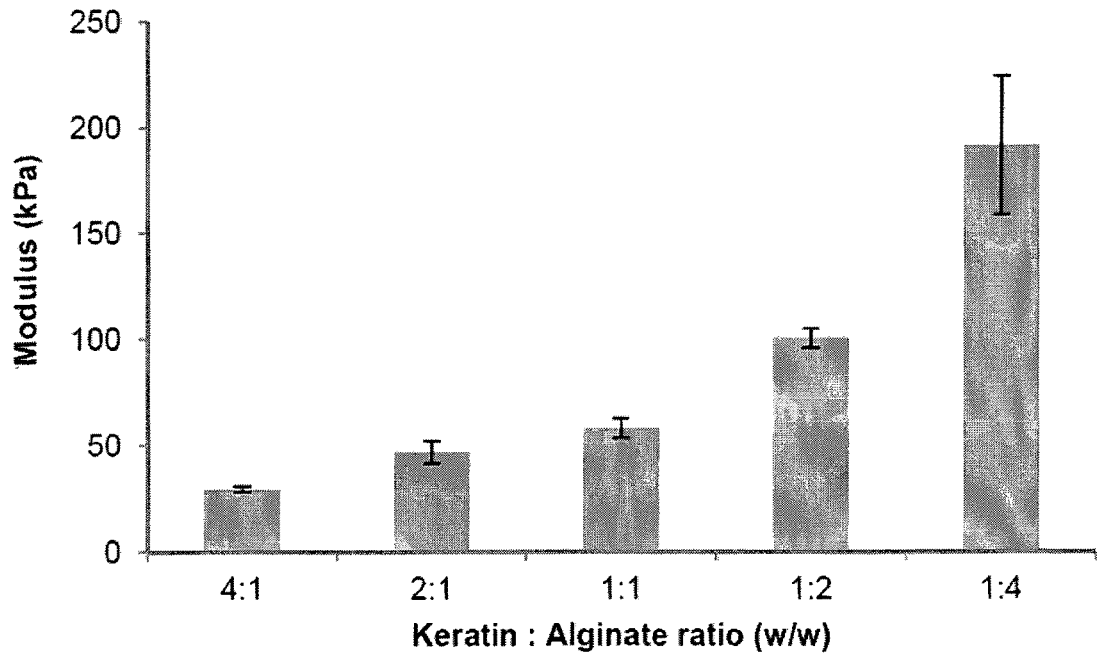
Figure 6:
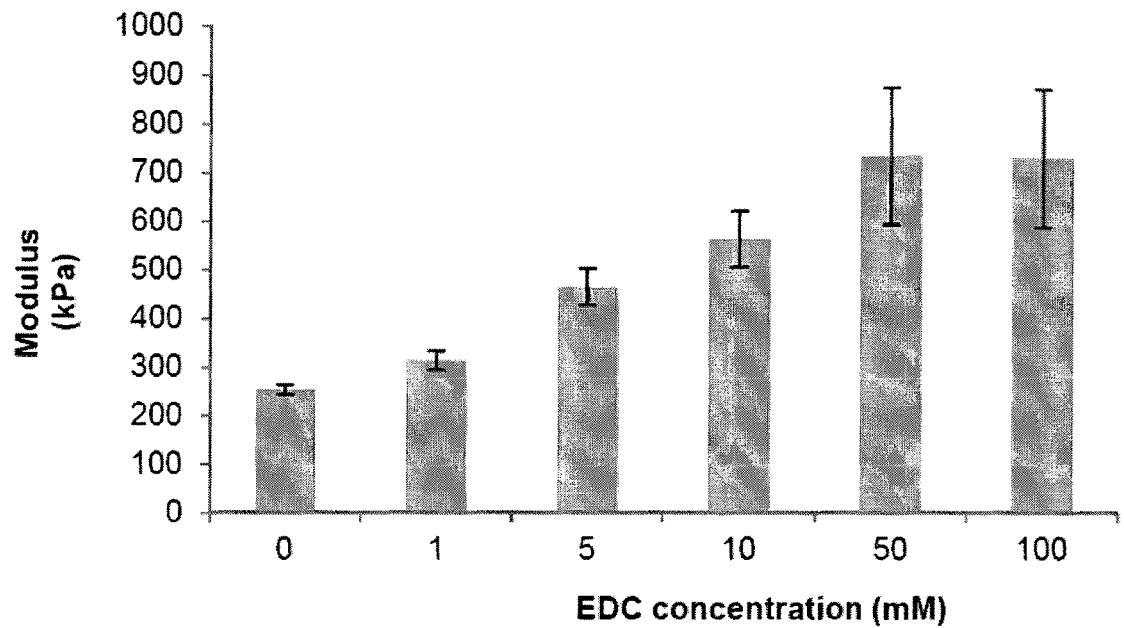
Figure 6:
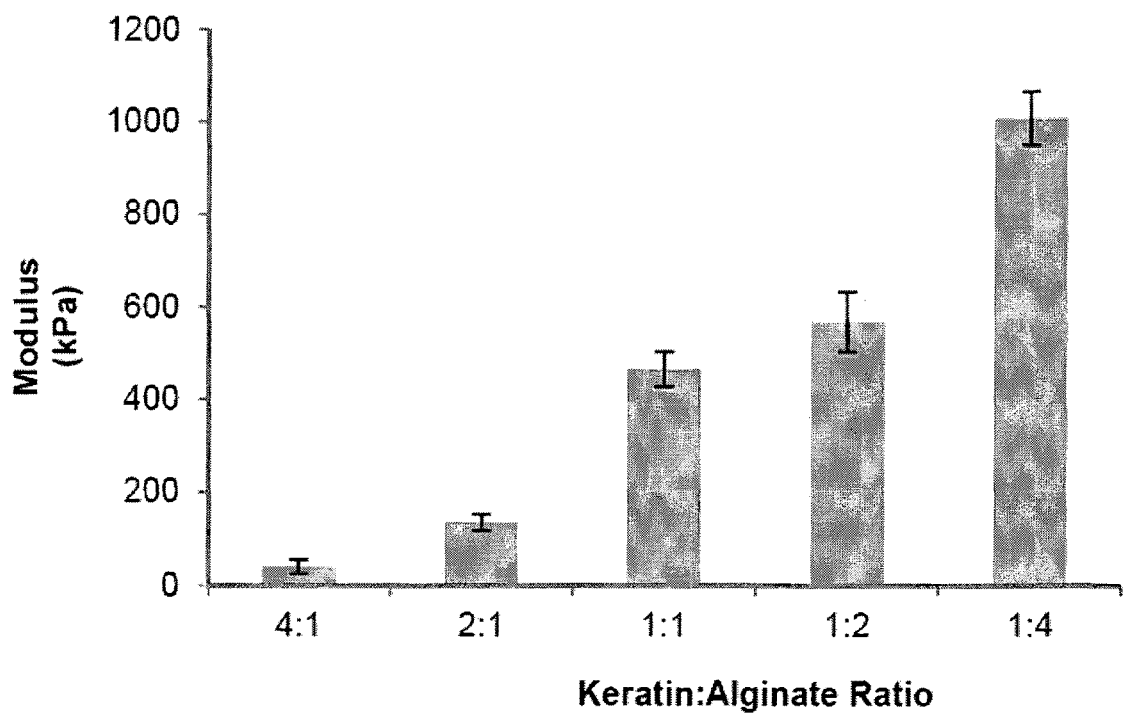

FIG. 6 are graphs showing (a) compression modulus; and (b) flexural modulus of crosslinked keratin-alginate sponges at (i) keratin to alginate ratio of 1:1 by weight and EDC concentrations of 0 mM, 1 mM, 5 mM, 10 mM, 50 mM and 100 mM; and (ii) EDC concentration of 10 mM and keratin-alginate ratios of 4:1, 2:1, 1:1, 1:2, and 1:4 by weight. The results revealed that with increasing concentration of EDC used, both compression and flexural moduli increased, i.e. crosslinking keratin and alginate improved the mechanical properties of the resulting matrix.

Figure 7:
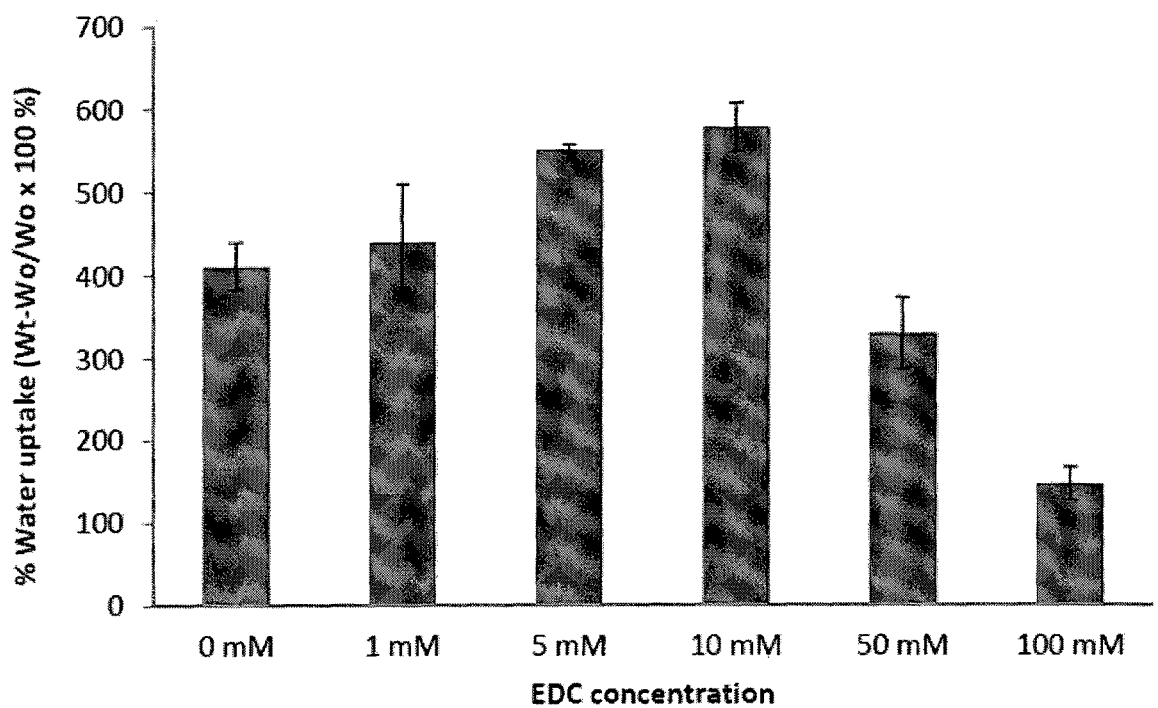

FIG. 7 is a graph showing water uptake of crosslinked keratin-alginate sponges with keratin to alginate ratio of 1:1 by weight and different concentrations of EDC (1 mM to 100 mM). Results show that with the crosslinking, keratin alginate sponges have the ability to uptake water up to 5 times its original weight (as shown by 5 mM and 10 mM EDC). This data also shows that a different crosslinking degree results in a different swelling capacity. Generally, as the degree of crosslinking increased, the swelling capacity of a material, and consequently the ability to uptake water, decreased.

Figure 8:
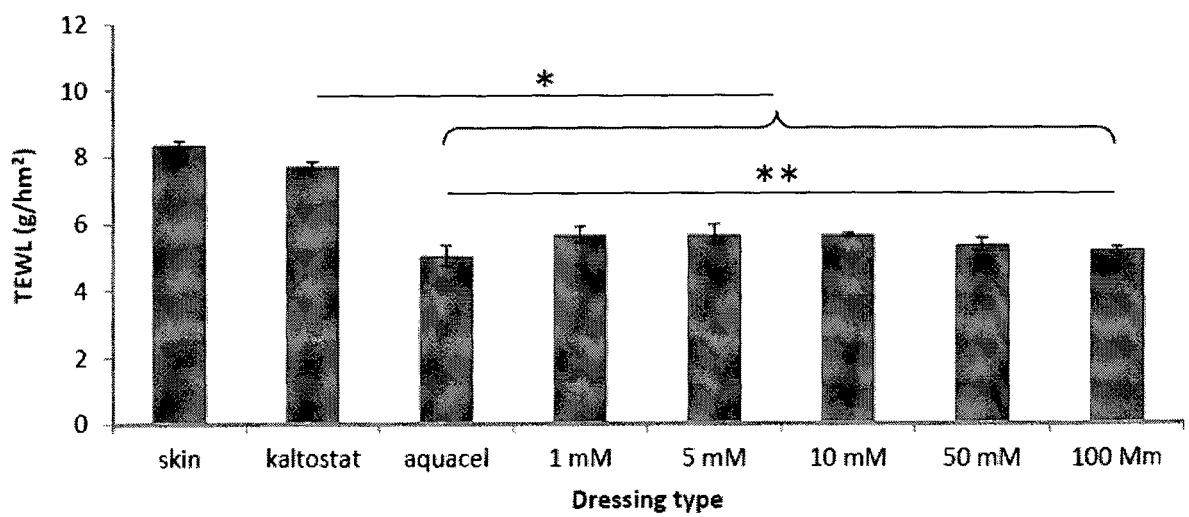

FIG. 8 is a graph showing water vapor transmission rate (WVTR) of crosslinked keratin-alginate sponges with different EDC concentration and with keratin to alginate ratio of 1:1 by weight in comparison to Aquacel™ and Kaltostat™. A comparable trend of WVTR across the different types of keratin-alginate sponges was observed. Overall, crosslinked sponges exhibited reduced water WVTR compared to Kaltostat™ (commercial alginate dressing) and comparable WVTR with Aquacel™ (commercial hydrofiber dressing for enhancing moist healing). *$p<0.05$ (1-way Analysis of Variance (ANOVA) followed by Student's t-test); **$p>0.05$ (1-way ANOVA).

Figure 9:
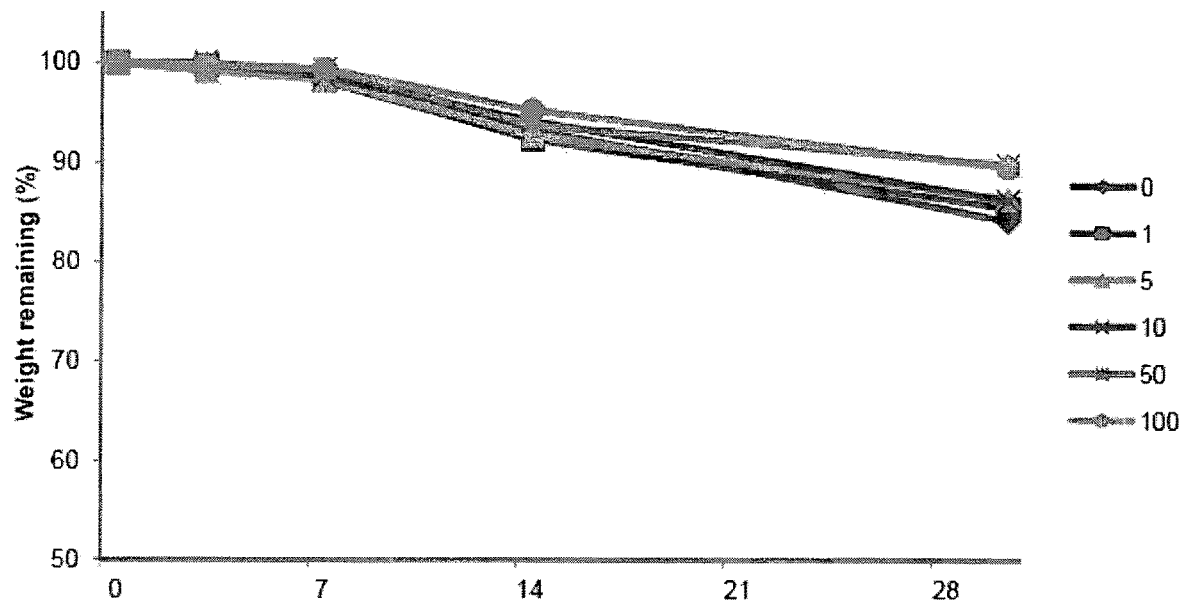
Figure 9:
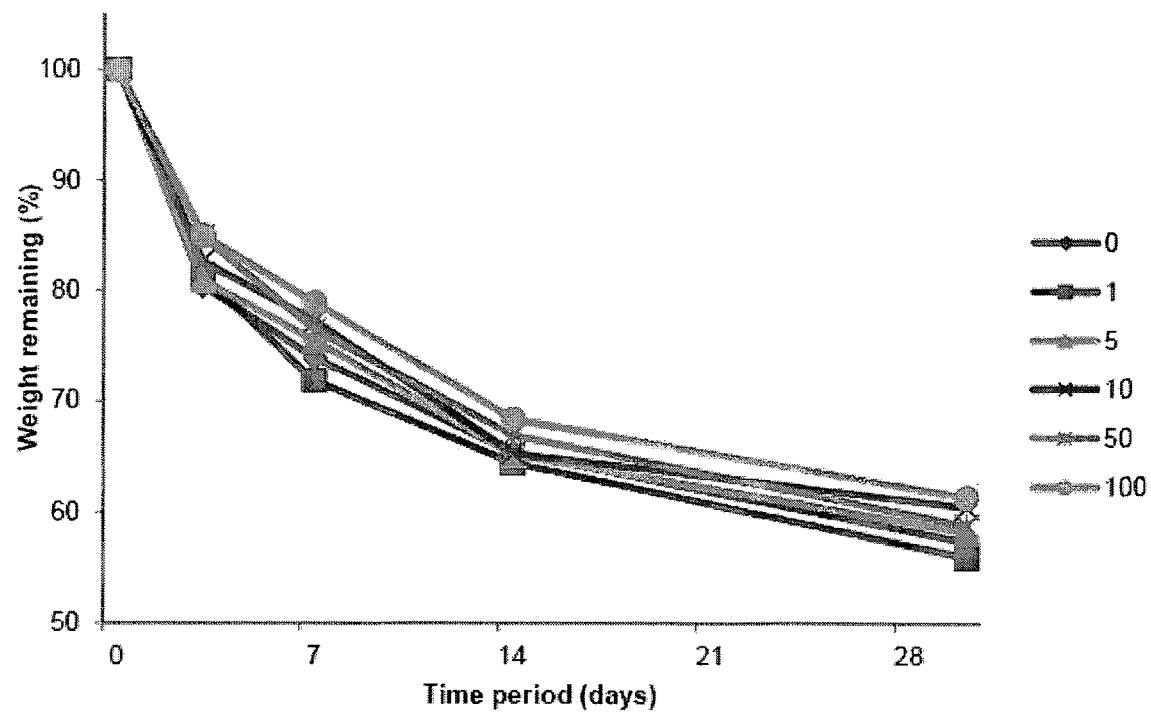
Figure 9:
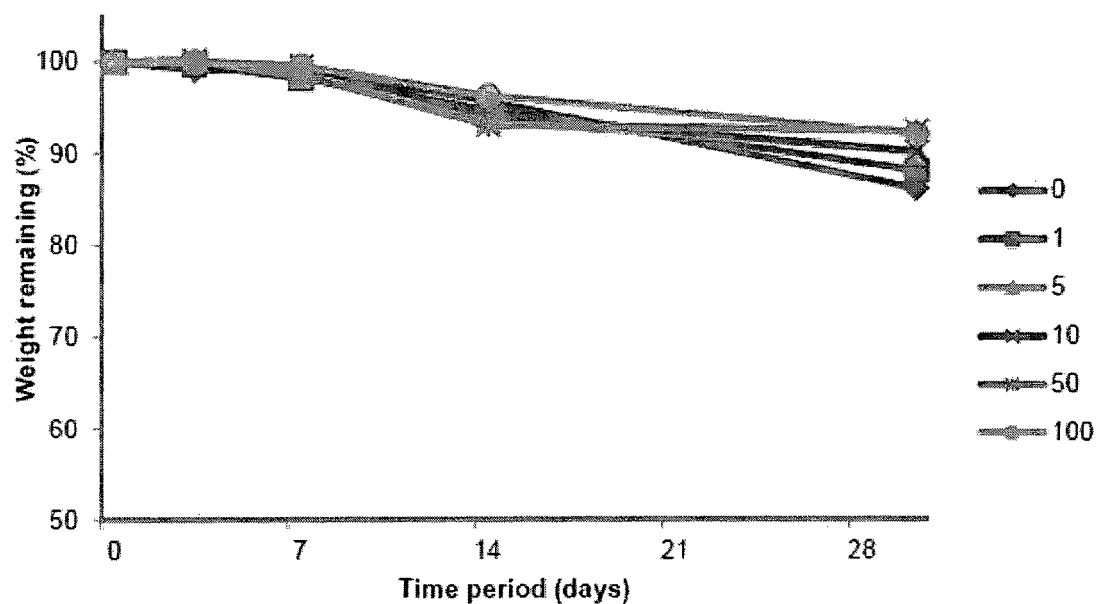

FIG. 9 depicts graphs of degradation of crosslinked keratin-alginate sponges with keratin to alginate ratio of 1:1 by weight and with different concentration of EDC (1 mM to 100 mM) using (a) Chymotrypsin, (b) Proteinase K, and (c) buffer. The results revealed that the sponges were generally resistant to aqueous hydrolysis and degradation by chymotrypsin. Proteinase K resulted in about 40% degradation after 30 days.

Figure 10:
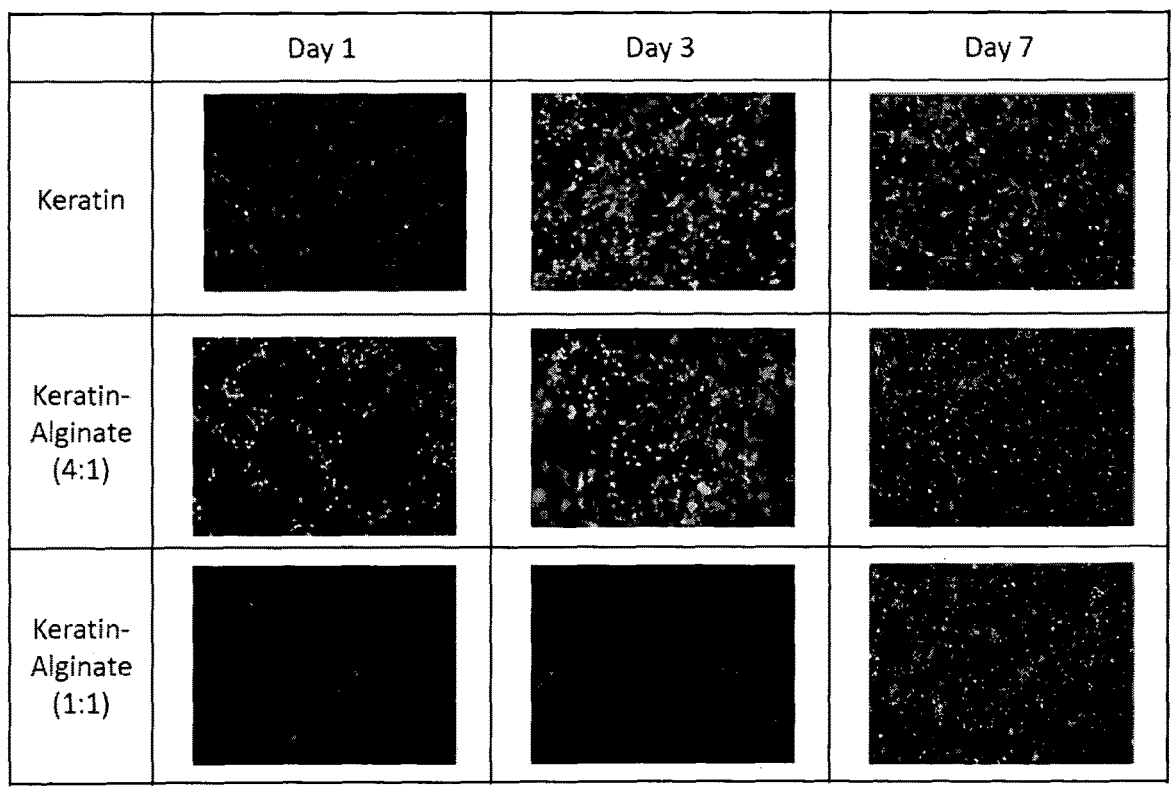
Figure 10:
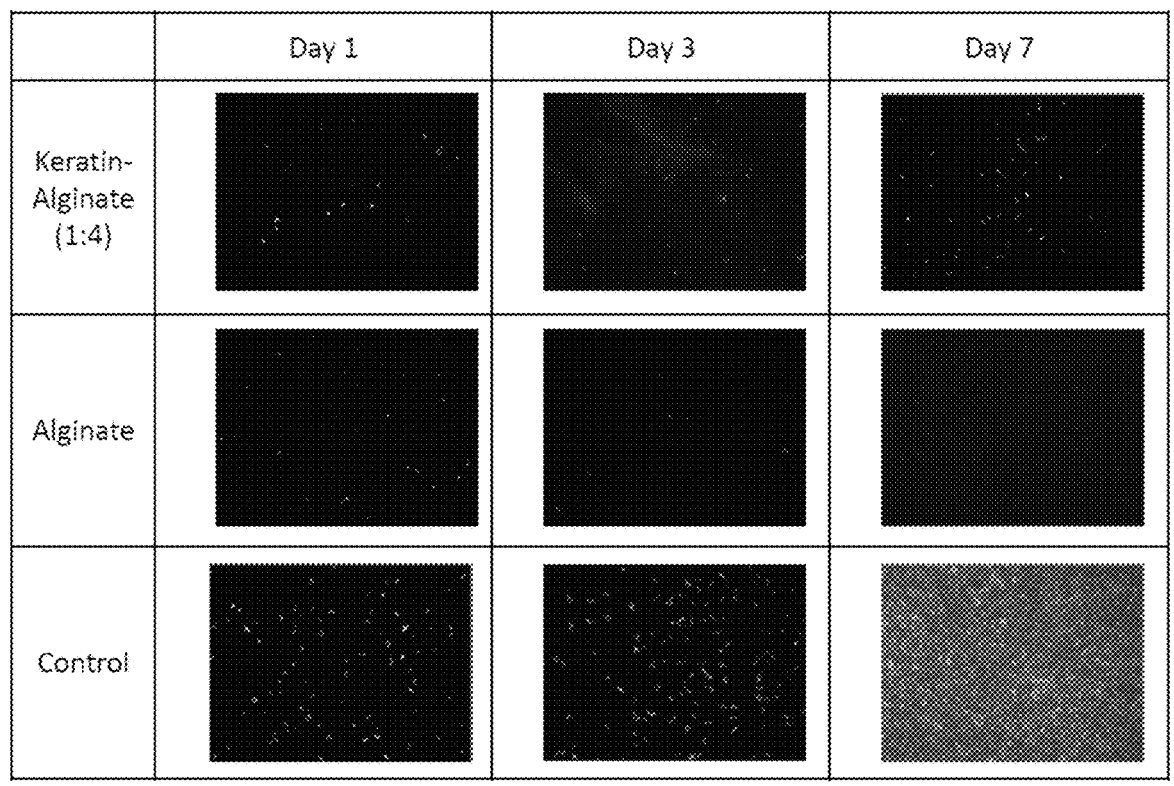

FIG. 10 depicts live-dead images of mouse fibroblasts (L929) cultured on crosslinked keratin-alginate (10 mM EDC concentration) coated Tissue Culture Polystyrene (TCPS) surfaces with different keratin-alginate ratio (2D). Fluorescent images were taken at indicated time points, showing that the majority of L929 fibroblasts remained viable over the culture period. Cell viability was higher on surfaces with increasing proportion of keratin.

Figure 11:
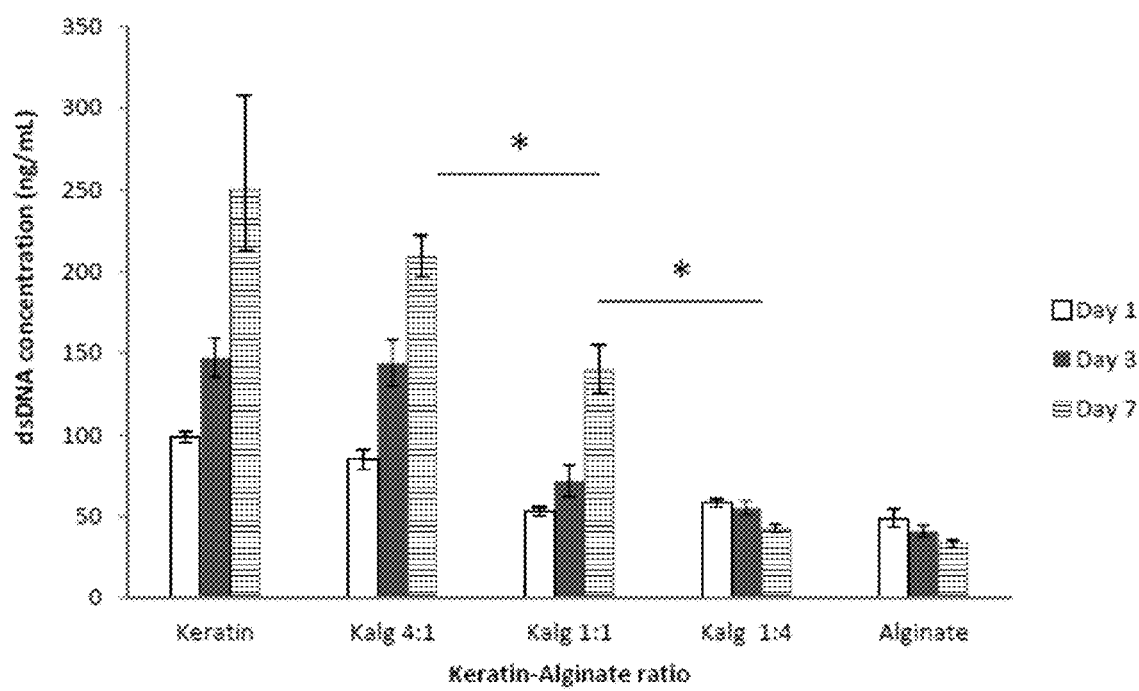

FIG. 11 is a graph showing double-stranded DNA quantification of L929 cells cultured on crosslinked keratin-alginate coated TCPS surfaces using 10 mM EDC concentration with different keratin-alginate ratio (2D). Results confirmed that cell proliferation increased on coated surfaces containing higher proportions of keratin. *$p<0.05$; comparison of Day 7 data across different sample groups based on Student's t-test.

Figure 12:
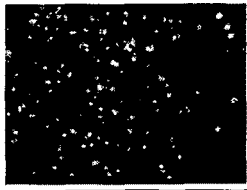
Figure 12:
Figure 12:
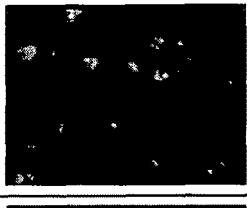
Figure 12:
Figure 12:
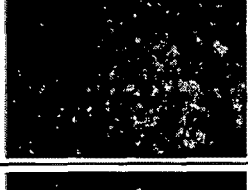
Figure 12:
Figure 12:

FIG. 12 depicts live-dead images of mouse fibroblasts (L929) cultured in 10 mM EDC crosslinked keratin-alginate sponges (3D) using keratin to alginate ratio of 1:1 by weight.

DETAILED DESCRIPTION

Biomaterials prepared by cross-linking keratin with a polymer having at least one of an amine and carboxylic acid functional group, such as alginate, via a carbodiimide-mediated reaction have been developed. In the exemplary embodiments shown, the cross-linked biomaterials prepared are porous and retain bioactivity of constituent materials. Advantageously, physical and mechanical properties of the keratin-based biomaterials, as compared to state of the art keratin-containing materials, are improved by the cross-linking reaction. Methods disclosed herein provide means of controlling mechanical properties of the keratin-based biomaterial formed, while retaining biochemical properties of the keratin and the polymer used to prepare the keratin-based biomaterial.

The invention refers accordingly in a first aspect to a method of preparing a keratin-based biomaterial. The term "keratin-based biomaterial" as used herein refers to a biocompatible substance containing keratin, whereby the term "biocompatible" refers to substances with minimal toxicity or irritation to biological tissue, and which is sufficiently tolerated by the body without adverse effects.

The keratin-based material comprises, consists essentially of, or consists of keratin. Keratin is a form of intermediate filament protein, and accounts for about three quarters of all known intermediate filament proteins in the human being. It is also the major component making up epithelial appendages such as hair and nails. Keratin possesses a high proportion of the two smallest amino acids, glycine and alanine, which allows sterically-unhindered hydrogen bonding between the amino and carboxyl groups of peptide bonds on adjacent protein chains, thereby facilitating their close alignment and strong binding. In addition, keratins have large amounts of the sulphur-containing amino acid cysteine, resulting in formation of disulfide bridges that act as permanent, thermal-stable cross-links to confer additional strength and rigidity to the filaments.

Method of the first aspect includes reacting keratin with a polymer having at least one of an amine and carboxylic functional group in the presence of a carbodiimide cross-linking agent to form a cross-linked keratin-polymer material.

In various embodiments, the keratin is obtained by incubating a keratin-containing material in a reducing agent or an oxidizing agent to extract keratin from the keratin-containing material. By incubating the keratin-containing material in a reducing agent or an oxidizing agent, the cross-linked structure of keratin in the keratin-containing material is broken down by either reduction or oxidation. In these reactions, the disulfide bonds in the sulphur-containing amino acid cysteine are cleaved, rendering the keratins soluble without appreciable disruption of amide bonds.

The keratin-containing material may comprise or consist of proteinaceous sources of keratin proteins from animal or human origin. Examples of keratin-containing material include, but are not limited to, wool, fur, skin, horns, hooves, beaks, feathers, and scales from animal origin; hair, nails and skin of human origin, and the like. In various embodiments, the keratin-containing material comprises or consists of human hair. Advantageously, human hair is biocompatible and renders its suitability for use with human subjects.

The reducing agent may be selected from the group consisting of sodium sulfide, sodium borohydride, 2-mercaptoethanol, tris(2-carboxyethyl)phosphine, dithiotreitiol, and mixtures thereof. The oxidizing agent may be selected from the group consisting of peracetic acid, hydrogen peroxide, performic acid, permanganate compounds, nitrate compounds such as nitric acid, halogens and halogens analogue compounds such as chlorine, bromine, chlorite, perchlorate, and mixtures thereof.

In embodiments in which a reducing agent is used, the resulting keratin may alternatively be referred to as a kerateine. In embodiments in which an oxidizing agent is used, the resulting keratin may alternatively be referred to as a keratose.

Generally, the keratin-containing material may be incubated for any suitable time period that allows extraction of keratin from the keratin-containing material. In various embodiments, incubating the keratin-containing material is carried out for a time period in the range of about 2 hours to about 10 hours, such as about 2 hours to about 8 hours, about 2 hours to about 6 hours, about 2 hours to about 4 hours, about 4 hours to about 10 hours, about 6 hours to about 10 hours, or about 8 hours to about 10 hours.

Incubating the keratin-containing material may be carried out at a temperature in the range of about 25° C. to about 50° C. For example, incubating the keratin-containing material may be carried out at a temperature in the range of about 25° C. to about 40° C., about 25° C. to about 35° C., about 25° C. to about 30° C., about 30° C. to about 50° C., about 35° C. to about 50° C., about 40° C. to about 50° C., about 25° C., about 30° C., or about 35° C. Advantageously, incubating the keratin-containing material may be carried out at ambient temperature and conditions. The term "ambient temperature" as used herein refers to a temperature of between about 20° C. to about 40° C.

Agitation, such as by stirring or ultrasonic agitation, may be used to maximize reduction or oxidation efficiency.

After incubation, the extracted keratin may be separated from residual matter of the keratin-containing material by separation techniques, such as filtration and centrifugation. In various embodiments, the keratin is rinsed using copious amounts of purified water, such that it is at least substantially free of residual reducing agent or oxidizing agent. In some embodiments, the extracted keratin is freeze dried prior to storage.

The method of the first aspect includes reacting keratin with a polymer having at least one of an amine and carboxylic functional group in the presence of a carbodiimide cross-linking agent to form a cross-linked keratin-polymer material.

The polymer having an amine and/or carboxylic functional group may have one or more amine functional groups, one or more carboxylic functional groups, or both amine and carboxylic functional groups. In various embodiments, the polymer having an amine and/or carboxylic functional group is selected from the group consisting of alginate, chitosan, gelatin, collagen, hyaluronic acid, fibrin, polyaminomethacrylate derivative, polylactic acid, polyglycolic acid, polyacrylamide, mixtures thereof, and copolymers thereof. Examples of copolymers having an amine and/or carboxylic functional group include, but are not limited to, poly(lactic-co-glycolic) acid (PLGA), and PLGA-grafted chitosan copolymers. In some embodiments, the polymer having an amine and/or carboxylic functional group comprises, or consists essentially of alginate. In specific embodiments, the polymer having an amine and/or carboxylic functional group is alginate.

As used herein, the term "carbodiimide cross-linking agent" refers to an organic compound having at least one carbodiimide functional group of formula —N=C=N—. Generally, any organic compounds containing a carbodiimide functional group may be used. In various embodiments, the carbodiimide cross-linking agent is water-soluble.

The carbodiimide cross-linking agent may, for example, be selected from the group consisting of 1-ethyl-3-(3-dimethylaminopropyl)carbodiimide, dicyclohexyl carbodiimide, and mixtures thereof. In specific embodiments, the carbodiimide cross-linking agent comprises or consists of 1-ethyl-3-(3-dimethylaminopropyl)carbodiimide.

In the presence of the carbodiimide cross-linking agent, carboxyl groups on the keratin or the polymer may be activated, which then react with amine groups on the keratin or the polymer to form an amide-linked conjugate. In so doing, the keratin is chemically cross-linked with the polymer to form the keratin-based biomaterial. Advantageously, the reaction may be carried out with or without pH adjustment. In various embodiments, the reaction is carried out in a buffered solution of pH 4 to pH 6, and a water-soluble carbodiimide is added to initiate the conjugation reaction.

In various embodiments, concentration of the carbodiimide cross-linking agent is in the range of about 1 mM to about 500 mM. For example, concentration of the carbodiimide cross-linking agent may be in the range of about 1 mM to about 250 mM, about 1 mM to about 150 mM, about 1 mM to about 100 mM, about 1 mM to about 50 mM, about 50 mM to about 500 mM, about 100 mM to about 500 mM, about 250 mM to about 500 mM, about 50 mM, about 100 mM, about 200 mM, about 300 mM, about 400 mM, or about 500 mM. In various embodiments, concentration of the carbodiimide cross-linking agent is in the range of about 50 mM to about 500 mM.

Weight ratio of the keratin to the polymer may be in the range of about 4:1 to about 1:4. For example, weight ratio of the keratin to the polymer may be about 1:1. Different ratios of keratin to polymer may be used to vary mechanical properties of the resulting cross-linked keratin-polymer material, which may in turn depend on the intended application. In specific embodiments, weight ratio of the keratin to the polymer is about 1:4. In one embodiment, the polymer is alginate, and weight ratio of the keratin to alginate is 1:4.

Method of the first aspect includes freeze drying the cross-linked keratin-polymer material to form the keratin-based biomaterial. Freeze drying, otherwise termed as lyophilisation, refers to a drying process in which a material is frozen to 0° C. or below, and with the surrounding pressure reduced, to allow frozen water in the material to sublimate. Accordingly, water in the cross-linked keratin-polymer material may be removed by freeze drying, and the keratin-based biomaterial thus prepared may be porous. In various embodiments, the keratin-based biomaterial is porous.

Porosity of the keratin-based biomaterial may be characterized by the size of the pores. According to the definition of the International Union of Pure, and Applied Chemistry (IUPAC), the term "mesopore/mesoporous" refers to pore size in the range of 2 nm to 50 nm; while a pore size below 2 nm is termed a micropore range, and a pore size that is greater than 50 nm is termed a macropore range. In various embodiments, the keratin-based biomaterial comprises or consists essentially of micropores.

Advantageously, methods of preparing a keratin-based biomaterial disclosed herein do not require specialized instruments for producing 3D porous templates due to simplicity in processing. This compares favorably to techniques such as wet spinning, which require specialized equipment and further processing to produce porous templates.

Furthermore, control of biomaterial properties may be achieved conveniently by adjusting concentration of the cross-linking agent, keratin and/or polymer. Resulting physical form of the cross-linked keratin-polymer biomaterial using methods of preparation disclosed herein is versatile, and may vary from thin films to thick sponges, and even hydrogels. This addresses issues with state of the art methods, such as particulate-leaching methods, that are limited to preparation of thin templates due to difficulties in leaching out porogens from thick templates.

In a second aspect, the invention relates to a keratin-based biomaterial prepared by a method according to the first aspect. The keratin-based biomaterial comprises keratin that is cross-linked with a polymer having an amine or carboxylic functional group using amide bonds. Examples of suitable polymers that may be used have already been described above.

Advantageously, physical and mechanical properties of the keratin-based biomaterials, as compared to state of the art keratin-containing material, are improved by the cross-linking reaction. In various embodiments, the cross-linked biomaterials prepared are porous, and retain bioactivity of constituent materials.

In various embodiments, the keratin-based biomaterial comprises keratin that is cross-linked with alginate using amide bonds. Keratin that is used to prepare the keratin-based biomaterial is highly abundant in nature, easily accessible, and may be processed easily. For example, keratin may be extracted from human hair. In embodiments in which alginate is used as the polymer, it may be extracted easily from algae. Advantageously, keratin-alginate sponges are good candidates as biomaterials, due to use of keratin derivable from human, and which may be autologous; and alginate, which is a material present in nature and which may be used to enhance wound healing.

Biomaterials prepared by methods disclosed herein may be used for applications, such as matrices for tissue engineering and regenerative medicine, for example, in cell and drug delivery; tissue fillers; wound dressings; and in vitro model for studying angiogenesis and cellular behavior in 3D.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

For illustration purposes, keratin-alginate sponges have been prepared. The biomaterials have controllable physical and mechanical properties to suit different applications. Such a template has not been reported before.

Example 1

Extraction of Keratin

Keratin is extracted from human hair using reducing agents, such as sodium sulfide, sodium borohydride, 2-mercaptoethanol, tris(2-carboxyethyl)phosphine, dithiotreitiol, or oxidizing agents, such as peracetic acid.

Finely cut human hair is dispersed in the reducing or oxidizing cocktails, and incubated for several hours at 40° C.

The resulting solution is filtered to remove hair debris. After filtering, the keratin solution is dialyzed exhaustively to remove remaining reducing or oxidizing agents. Finally, the human-hair keratin solution is freeze-dried and stored.

Example 2

Cross-Linking

The human-hair extracted keratin is subjected to chemical modification using selected carbodiimide cross-linker, such as 1-Ethyl-3-(3-dimethylaminopropyl)carbodiimide (EDC) and dicyclohexyl carbodiimide (DCC). Briefly, the extracted keratin solution is chemically cross-linked with alginate using a carbodiimide cross-linker, with or without pH adjustment.

The resulting cross-linked template is purified by dialysis and freeze-dried to yield a mechanically stable sponge. The cross-linked keratin-alginate sponges may be prepared in different ratios of keratin:alginate:cross-linker, in order to vary properties on the final template. Cross-linking of keratins with other materials may also be similarly carried out, as long as partner materials contain at least one of an amine and carboxylic group. Examples include natural polymers such as chitosan, hyaluronic acid, collagen, fibrin, or synthetic polymers, such as polyaminomethacrylate derivative, polylactic acid (PLA), polyglycolic acid (PGA), and polyacrylamide, as well as their co-polymers.

Example 3

Experimental Results

Porous sponges obtained from freeze-drying of keratin-alginate cross-linked with different concentrations of EDC have different physicochemical properties.

As shown in Table 1, increasing concentration of EDC resulted in an increase in the compression moduli of the sponges and a decrease in swelling index.

TABLE 1

Varying ratios of keratin, alginate, cross-linker, and associated water swelling index and compression modulus.

| | Keratin-Alginate final conc (% w/v) | EDC (mM) | Keratin-alginate ratio (w/w) | Swelling index (%) | Compression modulus (kPa) |
|---|---|---|---|---|---|
| A | 2 | 1 | 1:1 | 440.05 ± 69.90 | 14.28 ± 2.20 |
| B | 2 | 5 | 1:1 | 551.88 ± 5.46 | 11.75 ± 1.01 |
| C | 2 | 10 | 1:1 | 579.02 ± 29.65 | 15.43 ± 1.98 |
| D | 2 | 50 | 1:1 | 330.11 ± 42.95 | 31.35 ± 9.13 |
| E | 2 | 100 | 1:1 | 147.08 ± 20.06 | 41.98 ± 14.92 |

Figure 1:
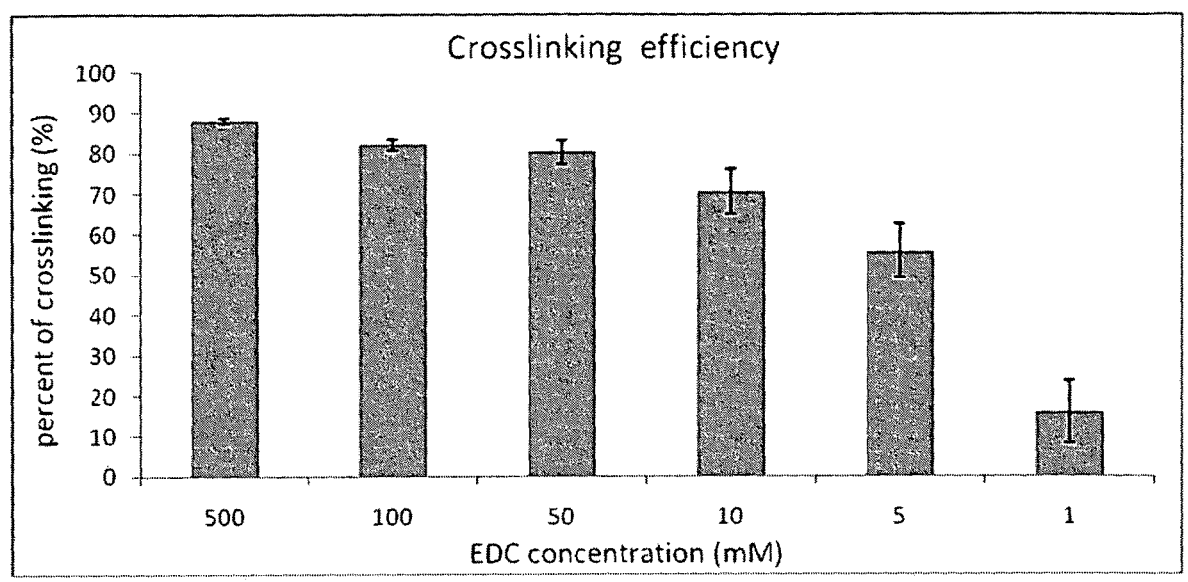
FIG. 1 is a graph showing efficiency of cross-linking keratin with alginate for keratin to alginate ratio of 1:1 by weight using varying concentrations of 1-ethyl-3-(3-dimethylaminopropyl)carbodiimide (EDC). Samples before and after cross-linking were pulverized and incubated with ninhydrin solution (4 mg/ml) at 90° C. for 20 min. Absorbance of the resulting solution was measured at 570 nm and the extent of cross-linking calculated using the following equation.

FIG. 1 is a graph showing efficiency of cross-linking keratin with alginate using varying concentrations of 1-Ethyl-3-(3-dimethylaminopropyl)carbodiimide (EDC). Degree of cross-linking was measured to reach about 80% when EDC concentrations of 50 mM and higher were used.

Cross-linking between keratin and alginate was also confirmed by the increased intensities of the amide bands in the infrared spectra, as shown in FIG. 2, which is a graph showing Fourier Transform Infrared Spectroscopy (FTIR) spectra of cross-linked keratin alginate at different EDC concentration. Macroscopically, the keratin-alginate sponges presented themselves as stable 3D sponges that took the shape of the holding vessel, as shown in FIG. 3. Microscopically, the cross-linked sponges had microporous architectures with pore spaces that were highly interconnected as shown in FIG. 4.

FIG. 5 depicts graphs of crosslinking index of crosslinked keratin-alginate sponges with different concentration of EDC from 1 mM to 100 mM based on (a) free amine group determination; and (b) carboxylic group determination. Ninhydrine was used for the detection of free amine bonds while methylene blue was used for the detection of free carboxylic acid groups. Both were measured with a spectrophotometer to calculate the remaining free groups. As shown in the graphs, the higher the EDC concentration used, the lower the remaining free amine and carboxylic acid groups compared to the non-crosslinked mixture, indicating that the degree of crosslinking increases with increasing amount of crosslinking agent used.

FIG. 6 are graphs showing (a) compression modulus; and (b) flexural modulus of crosslinked keratin-alginate sponges at various EDC concentrations from 0 mM to 100 mM; and various keratin-alginate ratios from 4:1 to 1:4. The compression and flexural moduli were measured by using Instron mechanical tester 5567 (Instron co., Massachusets). The moduli were determined by calculating the slope of the stress-strain curve using the Bluehill software. From the graphs, it may be seen that an increasing concentration of EDC increases both compression and flexural moduli, i.e. crosslinking keratin and alginate improved the mechanical properties of the resulting matrix. Further, a keratin:alginate ratio of 1:4 showed the highest compression and flexural moduli values.

FIG. 7 is a graph showing water uptake of crosslinked keratin-alginate sponges with different concentrations of EDC (1 mM to 100 mM). Water uptake was measured by measuring sample mass difference before and after immersing in deionized water for one minute and expressing this as a percentage of the original mass. Results show that with crosslinking, keratin alginate sponges have the ability to uptake water up to 5 times its original weight, such as that shown by 5 mM and 10 mM EDC. This data also demonstrates a different crosslinking degree results in a different swelling capacity. Generally, as the degree of crosslinking increased, the swelling capacity of a material, and consequently the ability to uptake water, decreased.

FIG. 8 is a graph showing water vapor transmission rate of crosslinked keratin-alginate sponges with different EDC concentration and keratin-alginate ratio in comparison to Aquacel™ and Kaltostat™. Water vapor transmission rate (WVTR) was measured by quantifying Transepidermal Water Loss (TEWL), on top of healthy human skin (the back of the arm) using a Tewameter. A comparable trend of WVTR across the different types of keratin-alginate sponges was observed. Overall, crosslinked sponges exhibited reduced water WVTR compared to Kaltostat™ (commercial alginate dressing) and comparable WVTR with Aquacel™ (commercial hydrofiber dressing for enhancing moist healing).

FIG. 9 depicts graphs of degradation of crosslinked keratin-alginate sponges with different concentration of EDC (1 mM to 100 mM) using (a) Chymotrypsin, (b) Proteinase K, and (c) buffer. Sponges (approximately 4 mg) were put inside a cell insert, weighed, and subsequently mounted on 24-well plate. 1 mL of the respective enzyme solutions (1 IU/mL in tris buffer pH 8) was added in each well (350 μL inside of the insert, 650 outside of the insert). Samples were taken out at each time point and freeze-dried. The weights of the dried samples were then measured. Differences in dry weight before and after degradation were calculated to determine the amount of degradation over the corresponding time of treatment. The results revealed that the sponges were generally resistant to aqueous hydrolysis and degradation by chymotrypsin. Proteinase K resulted in about 40% degradation after 30 days.

FIG. 10 depicts live-dead images of mouse fibroblasts (L929) cultured on crosslinked keratin-alginate (10 mM EDC concentration) coated TCPS surfaces with different keratin-alginate ratio (2D). Cells were stained using a combination of Calcein AM and Propidium Iodide to differentiate between live (green) and dead (red) cells. Fluorescent images were taken at indicated time points, showing that the majority of L929 fibroblasts remained viable over the culture period. Cell viability was higher on surfaces with increasing proportion of keratin.

FIG. 11 is a graph showing double-stranded DNA quantification of L929 cells cultured on crosslinked keratin-alginate coated TCPS surfaces with different keratin-alginate ratio (2D). Double-stranded DNA quantification was carried out using the PicoGreen assay, as a correlation for viable cells. Results confirmed that cell proliferation increased on coated surfaces containing higher proportions of keratin. *$p<0.05$; comparison of Day 7 data across different sample groups based on Student's t-test.

FIG. 12 depicts live-dead images of mouse fibroblasts (L929) cultured in 10 mM EDC crosslinked keratin-alginate sponges (3D).

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of preparing a microporous keratin-based biomaterial, the method comprising:
    a) reacting keratin with a polymer having at least one of an amine and carboxylic functional group in the presence of a carbodiimide cross-linking agent to form an amide cross-linked keratin-polymer material, wherein the keratin being used to react with the polymer comprises cleaved disulfide bonds after having been extracted from a keratin-containing material by incubating the keratin-containing material with a reducing agent or an oxidizing agent, wherein the polymer having at least one of the amine and carboxylic functional group comprises an alginate, and wherein the keratin is present in a proportion greater than the alginate prior to the reacting; and
    b) freeze-drying the amide cross-linked keratin-polymer material to form the microporous keratin-based biomaterial.

2. The method according to claim 1, wherein the reducing agent is selected from the group consisting of sodium sulfide, sodium borohydride, 2-mercaptoethanol, tris(2-carboxyethyl)phosphine, dithiotreitiol, and mixtures thereof.

3. The method according to claim 1, wherein the oxidizing agent is selected from the group consisting of peracetic acid, hydrogen peroxide, performic acid, permanganate compounds, nitric acid, chlorine, bromine, chlorite, perchlorate, and mixtures thereof.

4. The method according to claim 1, wherein incubating the keratin-containing material is carried out for a time period in the range of about 2 hours to about 10 hours.

5. The method according to claim 1, wherein incubating the keratin-containing material is carried out at a temperature in the range of about 25° C. to about 50° C.

6. The method according to claim 1, wherein the polymer having at least one of an amine and carboxylic functional group further comprises chitosan, gelatin, collagen, hyaluronic acid, fibrin, polyaminomethacrylate derivative, polylactic acid, polyglycolic acid, polyacrylamide, mixtures thereof, or copolymers thereof.

7. The method according to claim 1, wherein the carbodiimide cross-linking agent is selected from the group consisting of 1-ethyl-3-(3-dimethylaminopropyl) carbodiimide, dicyclohexyl carbodiimide, and mixtures thereof.

8. The method according to claim 1, wherein the carbodiimide cross-linking agent has a concentration in the range of about 1 mM to about 500 mM.

9. The method according to claim 1, wherein the carbodiimide cross-linking agent has a concentration in the range of about 50 mM to about 500 mM.

* * * * *